(12) United States Patent
Wiemker et al.

(10) Patent No.: US 11,410,305 B2
(45) Date of Patent: Aug. 9, 2022

(54) APPARATUS FOR ITERATIVE MATERIAL DECOMPOSITION OF MULTISPECTRAL DATA

(71) Applicant: KONINKLIJKE PHILIPS N.V., Eindhoven (NL)

(72) Inventors: Rafael Wiemker, Kisdorf (DE); Jörg Sabczynski, Hamburg (DE); Tobias Klinder, Uelzen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 102 days.

(21) Appl. No.: 16/967,446

(22) PCT Filed: Feb. 1, 2019

(86) PCT No.: PCT/EP2019/052458
§ 371 (c)(1),
(2) Date: Aug. 5, 2020

(87) PCT Pub. No.: WO2019/158371
PCT Pub. Date: Aug. 22, 2019

(65) Prior Publication Data
US 2021/0035291 A1 Feb. 4, 2021

(30) Foreign Application Priority Data
Feb. 14, 2018 (EP) .................................... 18156735

(51) Int. Cl.
*G06T 7/00* (2017.01)
*G16H 30/40* (2018.01)
*G06T 5/00* (2006.01)

(52) U.S. Cl.
CPC ............ *G06T 7/0012* (2013.01); *G06T 5/002* (2013.01); *G16H 30/40* (2018.01); *G06T 2207/10036* (2013.01); *G06T 2207/10081* (2013.01)

(58) Field of Classification Search
None
See application file for complete search history.

(56) References Cited

U.S. PATENT DOCUMENTS

| | | |
|---|---|---|
| 7,844,095 B2 | 11/2010 | Marzendorfer |
| 2014/0010430 A1 | 1/2014 | Chandelier |
| 2015/0125055 A1 | 5/2015 | Gao |

OTHER PUBLICATIONS

Jolivot, R., Benezeth, Y., & Marzani, F. (2013). Skin parameter map retrieval from a dedicated multispectral imaging system applied to dermatology/cosmetology. International Journal of Biomedical Imaging, 2013, 1-15. https://doi.org/10.1155/2013/978289 (Year: 2013).*

(Continued)

*Primary Examiner* — Vu Le
*Assistant Examiner* — Courtney Joan Nelson
(74) *Attorney, Agent, or Firm* — Larry Liberchuk

(57) ABSTRACT

Iterative material decomposition of multispectral image data includes providing a plurality of spectral images of a region of interest comprising a body part and a plurality of sets of material coefficients for a plurality of materials. Each spectral image is decomposed into a plurality of material images and an offset image. At least one of the material images for each spectral image is manipulated on the basis of at least one topological constraint relating to the body part to determine for each spectral image an updated plurality of material images and an updated offset image. A plurality of spectral images is then recomposed from the corresponding updated plurality of material images and the updated offset. Intensities at image locations are compared, and the updated (Continued)

plurality of material images is modified. The steps are repeated until convergence, and at least one of the recomposed spectral images at convergence is output.

14 Claims, 6 Drawing Sheets

(56) References Cited

OTHER PUBLICATIONS

PCT International Search Report, International application No. PCT/EP2019/052458, dated Apr. 1, 2019.
Nasirudin R. et al., "Electronic Cleansing for CT Colonography Using Spectral-Driven Iterative Reconstruction", Progress in Biomedical Optics and Imaging, SPIE—International Society for Optical Engineering, Bellingham, WA, US, vol. 10134, Mar. 3, 2017 (Mar. 3, 2017), pp. 1013436-1013436, XP060086657.
Cai W. et al., "Electronic Cleansing in Fecal-Tagging Dual-Energy CT Colonography Based on Material Decomposition and Virtual Colon Tagging", IEEE Transactions on Biomedical Engineering, IEEE Service Center, PI Scataway, NJ, USA, vol. 62, No. 2, Feb. 1, 2015 (Feb. 1, 2015), pp. 754-765.
Tachibana R. et al., "Electronic cleansing for dual-energy CT colonography based on material decomposition and virtual monochromatic imaging", Proc SPIE Int Soc Opt Eng. Mar. 20, 2015; 9414: 94140Q.
Long Y. et al., "Multi-Material Decomposition Using Statistical Image Reconstruction in X-Ray CT", Proc. 2nd Int. Mtg. on image formation in X-ray CT (2012):413-416.
Mendonca P.R.S. et al., "Multi-Material Decomposition of Spectral CT Images." Proc. SPIE 7622, Medical Imaging 2010: Physics of Medical Imaging, 76221W (Mar. 22, 2010).
Mendonca P.R.S. et al., "A Flexible Method for Multi-Material Decomposition of Dual-Energy CT images." Medical Imaging, IEEE Transactions on Medical Imaging, vol. 33, No. 1, Jan. 2014, pp. 99-116.

* cited by examiner

APPARATUS FOR ITERATIVE MATERIAL DECOMPOSITION OF MULTISPECTRAL DATA

FIELD OF THE INVENTION

The present invention relates to an apparatus for iterative material decomposition of multispectral image data, to a system for iterative material decomposition of multispectral image data, to a method for iterative material decomposition of multispectral image data, as well as to a computer program element.

BACKGROUND OF THE INVENTION

The general background of this invention is the field of X-ray spectral computed tomography (CT). In a CT system an X-ray source emits X-ray radiation. The emitted radiation traverses an examination region with a subject or object located within and is detected by a detector array opposite the X-ray source. The detector array detects the radiation traversing the examination region and the subject and generates projection data, e.g. raw detector data or projection images. A reconstructor processes the projection data and reconstructs a volumetric image of the subject or object. X-ray Spectral CT is an imaging modality that extends the capabilities of a conventional CT system. Dual-Energy (DE) CT, which is a specific configuration of spectral CT, utilizes two attenuation values acquired simultaneously at two photon energies to solve the photoelectric and Compton contribution that consists of the mass attenuation coefficient of a material, and thus to identify an unknown material by its value of photoelectric and Compton contribution. This scheme works especially well in materials such as iodine that has k-edge energy close to the mean value of a diagnostic energy range. Because any two linearly independent sums of two basis functions span the entire attenuation coefficient space, any material can be represented by a linear combination of two other materials, so called basis materials, such as water and iodine. The basis material images provide new applications such as monochromatic image, material cancellation image, effective atomic number image and electron density image.

However, even though two principal materials suffice mathematically to span the entire spectral space in an ideal formulation, under real conditions more materials may be needed if noise is present, if spatial resolution is limited, and if certain boundary conditions are to be met, such as no concentrations below 0% or above 100%, topological shape constraints, etc.

There are several approaches to perform dual energy CT acquisition such as dual-source, fast kVp switching, and dual-layer detector configurations.

In addition, quantitative imaging is one of the current major trends in the medical imaging community. Spectral CT supports this trend, as the additional spectral information improves the quantitative information that can be measured about the scanned object and its material composition.

Such Multi Material Decomposition (MMD) is becoming a fundamental task for many clinical applications, in which the goal is often to characterize, detect and/or quantify the amount of a given material. MMD can be utilized to view tumours, lymph nodes and in a process called electronic colon cleansing. Electronic colon cleansing has been developed because polyps in the colon can possibly develop into colon cancer. It is therefore recommended for asymptomatic patients above a certain age to perform endoscopic inspection of the colon (colonoscopy), and to detect and assess possible polyps. Since the compliance with this screening is low, non-invasive virtual colonoscopy (VC) with CT was developed as an alternative. By employing Volume Rendering (VR) techniques, a virtual endoscopy rendering can be generated of the colon wall, yielding an image impression similar to the view of a real endoscope. One complication is that the colon may contain stool and fluid which could hide possible polyps. Instead of using laxatives for forced physical cleansing of the colon (which would further depress the screening compliance rate), electronic cleansing (EC) has been developed. For this, patient ingest a contrast agent prior to the CT scan, which stains the fluid and stool by giving it a higher density for X-rays, yielding higher Hounsfield units (HU) in the CT image volume (as well as a different spectrum). The materials such as those tagged by the contrast agent, can be suppressed from the CT volume by EC image processing algorithms utilizing MMD. Thus, in the cleansed image volume, tagged material can no longer hide polyps. The advantage of multispectral CT over conventional CT is that it yields additional information for each image point, since contrast-tagged material manifests differently than e.g. soft-tissue or bone, and can thus lead to improved electronic cleansing of tagged material.

However, MMD for DE CT is very challenging, because decomposition into numerous materials taking into account the limited resolution of scanners and noise is an ill posed problem. Thus, standard electronic cleansing (EC) on conventional (non-spectral) CT is known to produce artefacts at image locations where not enough information is available, in particular at three-way-material transition areas (where e.g. Air-SoftTissue-TaggedMaterial are touching), and for only minimally-prepared colonoscopies (with no or light use of laxatives), where a lot of stool and fluid remains in the colon. These cleansing artifacts can lead to overlooked polyps, as well as to false positive erroneous detection of polyps, resulting in over- and under-diagnosis.

Further information relating to MMD can be found in the following documents: Mendonça, Paulo R S, et al. "Multi-material decomposition of spectral CT images." SPIE Medical Imaging. International Society for Optics and Photonics, 2010; Long, Yong, and Jeffrey A. Fessler. "Multi-material decomposition using statistical image reconstruction in X-ray CT." Proc. 2nd Int. Mtg. on image formation in X-ray CT (2012): 413-6; and Mendonça, Paulo R S, Peter Lamb, and Dushyant V. Sahani. "A flexible method for multi-material decomposition of dual-energy CT images." Medical Imaging, IEEE Transactions on 33.1 (2014): 99-116.

SUMMARY OF THE INVENTION

It would be advantageous to have improved apparatus for iterative material decomposition of multispectral image data.

The object of the present invention is solved with the subject matter of the independent claims, wherein further embodiments are incorporated in the dependent claims. It should be noted that the following described aspects and examples of the invention apply also for the apparatus for iterative material decomposition of multispectral image data, the system for iterative material decomposition of multispectral image data, the method for iterative material decomposition of multispectral image data and for the computer program element and the computer readable medium.

According to a first aspect, there is provided an apparatus for iterative material decomposition of multispectral image data, comprising:

an input unit;
a processing unit; and
an output unit.

The input unit is configured to provide the processing unit with a plurality of spectral images of a region of interest comprising a body part. The input unit is configured also to provide the processing unit with a plurality of sets of material coefficients for a plurality of materials. For a set of material coefficients each material coefficient is associated with a corresponding material, and each set of material coefficients is associated with a corresponding spectral image of the plurality of spectral images. The processing unit is configured to:

i) decompose each spectral image of the plurality of spectral images into a plurality of material images and an offset image, wherein different material images correspond to different materials of the plurality of materials, and wherein a material image is represented by the material coefficient for the corresponding material multiplied by material concentrations at different image locations, and wherein the material coefficient is one of the material coefficients from the set of material coefficient for the corresponding spectral image;

ii) manipulate at least one of the material images for each spectral image on the basis of at least one topological constraint relating to the body part to determine for each spectral image an updated plurality of material images and an offset image;

iii) recompose a plurality of spectral images, wherein each recomposed spectral image is recomposed from the corresponding updated plurality of material images and the offset image;

iv) compare intensities at image locations in a recomposed spectral image to the intensities at the image locations in its corresponding spectral image prior to recomposition to determine a plurality of corrections, wherein a correction is associated with an image location;

v) modify the updated plurality of material images for each spectral image comprising utilization of the corresponding plurality of corrections;

vi) iterate ii) to v) until convergence; and

The output unit is configured to output at least one of the recomposed spectral images at convergence and/or output at least one of the updated material images at convergence.

In other words, a number K of spectral images are each decomposed into a number N of different base materials plus offsets. A location in an imaged object for one spectral image is represented by N+1 values, and this location in an imaged for a different spectral image is represented by N+1 values. Thus, the location in the imaged object is represented by K*(N+1) values. All locations in the imaged object are similarly represented by K*(N+1) values. Iterative application of topological constraints, for example shape constraints that remove implausible object configurations, to material images and comparison of images that are recomposed from these material images with images prior to decomposition enables imagery to iterate towards a solution where body parts can be more clearly resolved from surrounding material.

In this manner, for example electronic colon cleansing is provided from multispectral imagery and tumour and lymph node contrast uptake analysis and perfusion is enabled.

To put this another way, iterative shape constrained multi-material decomposition provides for improved image processing of acquired multispectral imagery of body parts.

To explain, further an exact solution of the K*(N+) values is not possible for all voxels, however as described a shape constrained multi-material decomposition and recomposition when applied iteratively enables a solution to derived.

In an example, each spectral image of the plurality of spectral images is decomposed into a linear combination of the plurality of material images and the offset image.

In an example, an offset associated with a first spectral image is different to an offset associated with a second spectral image.

In an example, the processing unit is configured to apply Gaussian smoothing to the recomposed plurality of spectral images.

In this way, the point spread function (PSF) of the X-ray scanner used to acquire the spectral images can be taken into account. Scanners have certain levels of resolution, which means that intensities in neighboring locations or voxels can spill into one another. The PSF of the scanner is then simulated in forward modelling by applying Gaussian smoothing to the synthesized (recomposed) energy (spectral) images. This obviates de-convolving the acquired energy images.

In an example, the processing unit is configured to analyze the at least one of the material images for each spectral image to determine connected components. The at least one topological constraint relating to the body part comprises that the body part is comprised of at least one connected component.

In this way, material which is "floating", such as stools in a colon can be determined as such and diminished or erased from imagery.

In an example, the at least one connected component is a single connected component.

In other words, knowledge that a body part such as a colon wall is a single connected component, can be used to manipulate a material image. Also, this enables free floating islands of material not to be considered as forming the body part because this is not anatomically plausible. Additionally, holes can be discounted.

In an example, manipulation of the at least one of the material images on the basis of the at least one topological constraint comprises setting material coefficients other than those for the at least one connected component to zero.

In this manner, images can be iteratively cleaned to leave the features such as a colon wall or stained tumor or lymph node present;

In an example, manipulation of the at least one of the material images on the basis of the at least one topological constraint comprises setting material coefficients other than those for the largest connected component to zero.

In an example, the processing unit is configured to calculate a plurality of gradients between intensities at a corresponding plurality of locations in the spectral image prior to recomposition. The processing unit is configured to utilize the plurality of gradients with the recomposed spectral image to determine a plurality of gradient derived corrections, and wherein modification of the updated plurality of material images for each spectral image comprises utilization of the corresponding plurality of gradient derived corrections.

In this manner, gradients provide an additional source of information in aiding the solution of an ill-posed problem.

In an example, the processing unit is configured to determine a plurality of gradients in intensity between a plurality of first locations and a plurality of second locations in the spectral image prior to recomposition and apply the plurality of gradients to the plurality of first locations in the recomposed spectral image to determine a plurality of gradient derived intensities at the plurality of second locations in the recomposed spectral image. Determination of the plurality of gradient derived corrections then comprises a comparison of the plurality of gradient derived intensities at the plurality of second locations in the recomposed image with a plurality of intensities at the plurality of second locations in the recomposed spectral image.

In an example, the comparison of the plurality of gradient derived intensities at the plurality of second locations in the recomposed image with the plurality of intensities at the plurality of second locations in the recomposed spectral image comprises a subtraction of the gradient derived intensities at the plurality of second locations in the recomposed image from the plurality of intensities at the plurality of second locations in the recomposed spectral image to provide a plurality of intensity corrections. Modification of the updated plurality of material images for each spectral image comprises correcting the plurality of intensities at the plurality of first positions in the recomposed image by the corresponding plurality of intensity corrections and multiplication of the corrected intensities by the material coefficient for each material image of the updated plurality of material images for each spectral image.

In an example, decomposition of each spectral image of the plurality of spectral images into a plurality of material images and an offset image comprises the enforcement of a concentration constraint such that the summation of material concentrations at a location in the plurality of spectral images is less than or equal to one.

According to a second aspect, there is provided a medical system for iterative material decomposition of multispectral image data, comprising:
an image acquisition unit; and
an apparatus for iterative material decomposition of multispectral image data according to the first aspect.

The image acquisition unit is configured to acquire the plurality of spectral X-ray images of the region of interest comprising the body part.

According to a third aspect, there is provided a method for iterative material decomposition of multispectral image data, comprising:
a) providing a plurality of spectral images of a region of interest comprising a body part;
b) providing a plurality of sets of material coefficients for a plurality of materials, wherein for a set of material coefficients each material coefficient is associated with a corresponding material, and wherein each set of material coefficients is associated with a corresponding spectral image of the plurality of spectral images;
c) decomposing each spectral image of the plurality of spectral images into a plurality of material images and an offset image, wherein different material images correspond to different materials of the plurality of materials, and wherein a material image is represented by the material coefficient for the corresponding material multiplied by material concentrations at different image locations, and wherein the material coefficient is one of the material coefficients from the set of material coefficient for the corresponding spectral image;
e) manipulating at least one of the material images for each spectral image on the basis of at least one topological constraint relating to the body part to determine for each spectral image an updated plurality of material images and an offset image;
f) recomposing a plurality of spectral images, wherein each recomposed spectral image is recomposed from the corresponding updated plurality of material images and the offset image;
g) comparing intensities at image locations in a recomposed spectral image to the intensities at the image locations in its corresponding spectral image prior to recomposition to determine a plurality of corrections, wherein a correction is associated with an image location;
i) modifying the updated plurality of material images for each spectral image comprising utilization of the corresponding plurality of corrections;
j) iterating steps e) to i) until convergence; and
k) outputting at least one of the recomposed spectral images at convergence and/or output at least one of the updated material images at convergence.

According to another aspect, there is provided a computer program element controlling apparatus as previously described which, in the computer program element is executed by processing unit, is adapted to perform the method steps as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
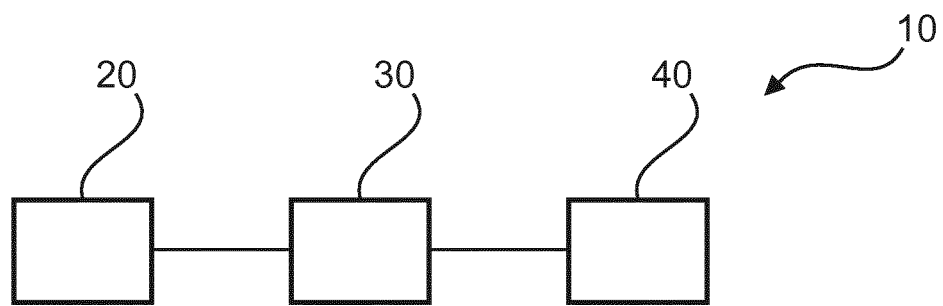
FIG. 1 shows a schematic set up of an example of an apparatus for iterative material decomposition of multispectral image data.

FIG. 1 shows an example of an apparatus 10 for iterative material decomposition of multispectral image data. The apparatus 10 comprises an input unit 20, a processing unit 30, and an output unit 40. The input unit 20 is configured to provide the processing unit 30 with a plurality of spectral images of a region of interest comprising a body part. The input unit 20 is configured also to provide the processing unit 30 with a plurality of sets of material coefficients for a plurality of materials. For a set of material coefficients each material coefficient is associated with a corresponding material, and each set of material coefficients is associated with a corresponding spectral image of the plurality of spectral images. The processing unit 30 is configured to:

i) decompose each spectral image of the plurality of spectral images into a plurality of material images and an offset image. Different material images correspond to different materials of the plurality of materials, and a material image is represented by the material coefficient for the corresponding material multiplied by material concentrations at different image locations, and the material coefficient is one of the material coefficients from the set of material coefficient for the corresponding spectral image;

ii) manipulate at least one of the material images for each spectral image on the basis of at least one topological constraint relating to the body part to determine for each spectral image an updated plurality of material images and an offset image;

iii) recompose a plurality of spectral images, wherein each recomposed spectral image is recomposed from the corresponding updated plurality of material images and the offset image;

iv) compare intensities at image locations in a recomposed spectral image to the intensities at the image locations in its corresponding spectral image prior to recomposition to determine a plurality of corrections, wherein a correction is associated with an image location;

v) modify the updated plurality of material images for each spectral image comprising utilization of the corresponding plurality of corrections;

vi) iterate ii) to v) until convergence.

The output unit 40 is configured to output at least one of the recomposed spectral images at convergence and/or output at least one of the updated material images at convergence.

In an example, the plurality of spectral images comprises an image that is a combination of two or more spectrally resolved images. Thus, this image can be an attenuation or non-spectrally resolved image.

In an example, the plurality of spectral images comprises a plurality of images derived from spectral images such as a Photoelectric scattering total attenuation coefficient image and a Compton scattering total attenuation coefficient image.

In an example, an image location is a volume pixel or voxel.

In an example, a contrast agent is present in the region of interest.

In an example, the body part is a colon or part of a colon. In other words, multispectral image decomposition is used in an iterative manner with utilization of topological constraints, enabling the body part to be separated from surrounding material. In this manner, improved electronic colon cleansing is provided.

In an example, the body part is a tumour or lymph node. Thus, when a contrast agent is injected, for the appraisal of a tumour or lymph node it is important to consider the uptake pattern and intensity of the contrast agent. The iterative decomposition apparatus described here enables the contrast material image to be reconstructed as precisely as possible.

According to an example, each spectral image of the plurality of spectral images is decomposed into a linear combination of the plurality of material images and the offset image.

According to an example, an offset associated with a first spectral image is different to an offset associated with a second spectral image.

According to an example, the processing unit is configured to apply Gaussian smoothing to the recomposed plurality of spectral images.

According to an example, the processing unit is configured to analyze the at least one of the material images for each spectral image to determine connected components. The at least one topological constraint relating to the body part then comprises that the body part is comprised of at least one connected component.

According to an example, the at least one connected component is a single connected component.

According to an example, manipulation of the at least one of the material images on the basis of the at least one topological constraint comprises setting material coefficients other than those for the at least one connected component to zero.

According to an example, manipulation of the at least one of the material images on the basis of the at least one topological constraint comprises setting material coefficients other than those for the largest connected component to zero.

According to an example, the processing unit is configured to calculate a plurality of gradients between intensities at a corresponding plurality of locations in the spectral image prior to recomposition. The processing unit is configured also to utilize the plurality of gradients with the recomposed spectral image to determine a plurality of gradient derived corrections. Modification of the updated plurality of material images for each spectral image comprises utilization of the corresponding plurality of gradient derived corrections.

According to an example, the processing unit is configured to determine a plurality of gradients in intensity between a plurality of first locations and a plurality of second locations in the spectral image prior to recomposition. The processing unit is configured also to apply the plurality of gradients to the plurality of first locations in the recomposed spectral image to determine a plurality of gradient derived intensities at the plurality of second locations in the recomposed spectral image. Determination of the plurality of gradient derived corrections comprises a comparison of the plurality of gradient derived intensities at the plurality of second locations in the recomposed image with a plurality of intensities at the plurality of second locations in the recomposed spectral image.

According to an example, the comparison of the plurality of gradient derived intensities at the plurality of second locations in the recomposed image with the plurality of intensities at the plurality of second locations in the recomposed spectral image comprises a subtraction of the gradient derived intensities at the plurality of second locations in the recomposed image from the plurality of intensities at the plurality of second locations in the recomposed spectral image to provide a plurality of intensity corrections. Modification of the updated plurality of material images for each spectral image comprises correcting the plurality of intensities at the plurality of first positions in the recomposed image by the corresponding plurality of intensity corrections and multiplication of the corrected intensities by the material coefficient for each material image of the updated plurality of material images for each spectral image.

In an example, an intensity correction is subtracted from an intensity at a first position and the resulting value is multiplied by the material coefficient for each material image.

According to an example, decomposition of each spectral image of the plurality of spectral images into a plurality of material images and an offset image comprises the enforcement of a concentration constraint such that the summation of material concentrations at a location in the plurality of spectral images is less than or equal to one.

In an example, when the summation of material concentrations at the location in the plurality of spectral images is greater than one, enforcement of the concentration constraint comprises a division of each material concentration by the summation of material concentrations.

In an example, decomposition of each spectral image of the plurality of spectral images into a plurality of material images and an offset image comprises enforcing a concentration constraint, wherein material concentrations at different image locations must be greater than or equal to zero.

Figure 2:
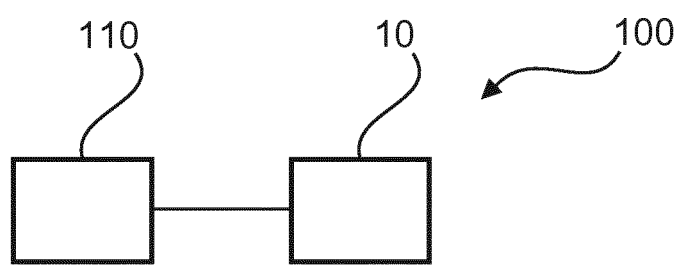
FIG. 2 shows a schematic set up of an example of a system for iterative material decomposition of multispectral image data.

FIG. 2 shows an example of a medical system 100 for iterative material decomposition of multispectral image data. The system comprises an image acquisition unit 110, and an apparatus 10 for iterative material decomposition of multispectral image data as described with respect to any examples of FIG. 1. The image acquisition unit 110 is configured to acquire the plurality of spectral X-ray images of the region of interest comprising the body part.

In an example, the image acquisition unit comprises an X-ray imaging device, for example, a tomosynthesis arrangement.

Figure 3:
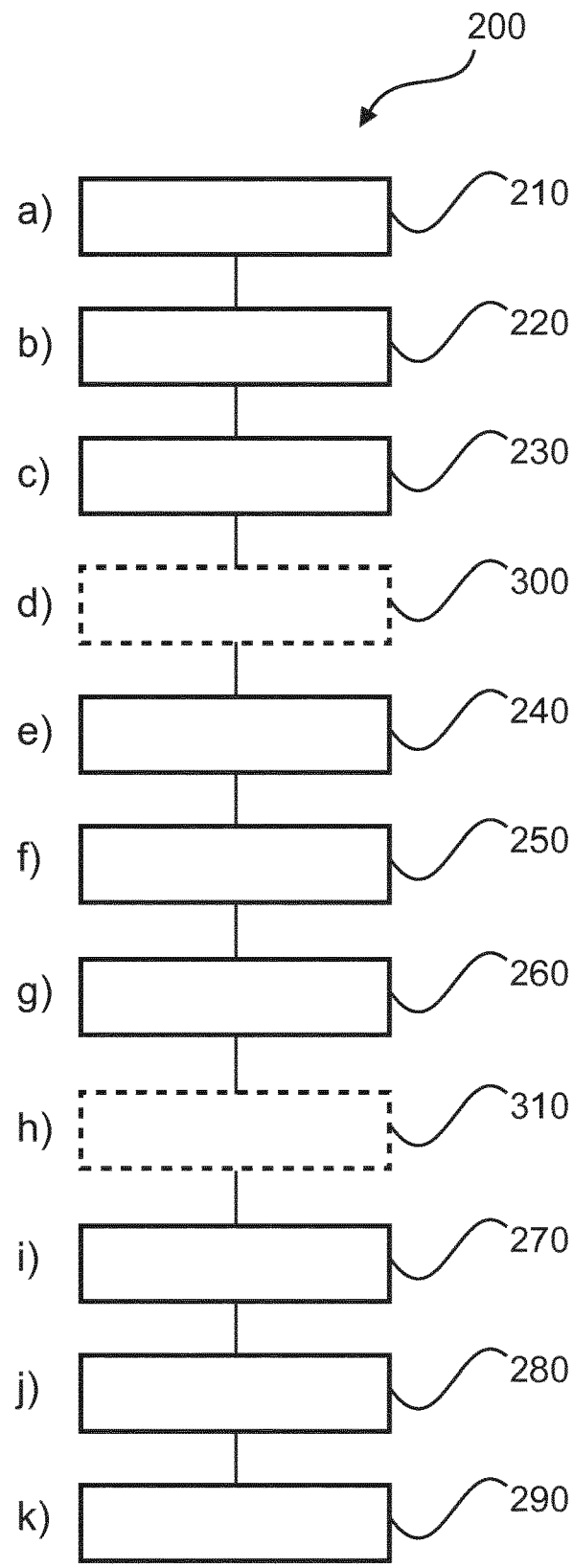
FIG. 3 shows a method for iterative material decomposition of multispectral image data.

FIG. 3 shows a method 200 for iterative material decomposition of multispectral image data in its basic steps. The method 200 comprises:

in a providing step 210, also referred to as step a), providing a plurality of spectral images of a region of interest comprising a body part;

in a providing step 220, also referred to as step b), providing a plurality of sets of material coefficients for a plurality of materials. For a set of material coefficients each material coefficient is associated with a corresponding material, and each set of material coefficients is associated with a corresponding spectral image of the plurality of spectral images;

in a decomposing step 230, also referred to as step c), decomposing each spectral image of the plurality of spectral images into a plurality of material images and an offset image. Different material images correspond to different materials of the plurality of materials. A material image is represented by the material coefficient for the corresponding material multiplied by material concentrations at different image locations, and the material coefficient is one of the material coefficients from the set of material coefficient for the corresponding spectral image;

in a manipulating step 240, also referred to as step e), manipulating at least one of the material images for each spectral image on the basis of at least one topological constraint relating to the body part to determine for each spectral image an updated plurality of material images and an offset image;

in a recomposing step 250, also referred to as step f), recomposing a plurality of spectral images, wherein each recomposed spectral image is recomposed from the corresponding updated plurality of material images and the offset image;

in a comparing step 260, also referred to as step g), comparing intensities at image locations in a recomposed spectral image to the intensities at the image locations in its corresponding spectral image prior to recomposition to determine a plurality of corrections, wherein a correction is associated with an image location;

in a modifying step 270, also referred to as step i), modifying the updated plurality of material images for each spectral image comprising utilization of the corresponding plurality of corrections;

in an iterating step 280, also referred to as step j), iterating steps e) to i) until convergence; and in an outputting step 290, also referred to as step k), outputting at least one of the recomposed spectral images at convergence and/or output at least one of the updated material images at convergence.

In an example, convergence occurs when in step g) there is a small mean shift in material images after modification.

In an example, each spectral image of the plurality of spectral images is decomposed into a linear combination of the plurality of material images and the offset image.

In an example, an offset associated with a first spectral image is different from an offset associated with a second spectral image.

In an example, Gaussian smoothing is applied to the recomposed plurality of spectral images.

In an example, the method comprises step d) analyzing (300) the at least one of the material images for each spectral image to determine connected components, and wherein step e) comprises that the body part is comprised of at least one connected component.

In an example, the at least one connected component is a single connected component.

In an example, step e) comprises setting material coefficients other than those for the at least one connected component to zero.

In an example, step e) comprises setting material coefficients other than those for the largest connected component to zero.

In an example, the method comprises step h) calculating 310 a plurality of gradients between intensities at a corresponding plurality of locations in the spectral image prior to recomposition. The method then comprises utilizing the plurality of gradients with the recomposed spectral image to determine a plurality of gradient derived corrections. Step i) then comprises utilization of the corresponding plurality of gradient derived corrections.

In an example, step h) comprises determining a plurality of gradients in intensity between a plurality of first and second locations in the spectral image prior to recomposition. The method then comprises applying the plurality of gradients to the plurality of first locations in the recomposed spectral image to determine a plurality of gradient derived intensities at the plurality of second locations in the recomposed spectral image. Determination of the plurality of gradient derived corrections then comprises comparing the plurality of gradient derived intensities at the plurality of second locations in the recomposed image with a plurality of intensities at the plurality of second locations in the recomposed spectral image.

In an example, in step h) comparing the plurality of gradient derived intensities at the plurality of second locations in the recomposed image with the plurality of intensities at the plurality of second locations in the recomposed spectral image comprises subtracting the gradient derived intensities at the plurality of second locations in the recomposed image from the plurality of intensities at the plurality of second locations in the recomposed spectral image to provide a plurality of intensity corrections. Step i) then comprises correcting the plurality of intensities at the plurality of first positions in the recomposed image by the corresponding plurality of intensity corrections and multiplication of the corrected intensities by the material coefficient for each material image of the updated plurality of material images for each spectral image.

In an example, step c) comprises enforcing a concentration constraint such that the summation of material concentrations at a location in the plurality of spectral images is less than or equal to one.

In this manner an algorithm applying the method can be applied to imagery of body parts as well as to phantoms.

The apparatus, system and method for iterative material decomposition of multispectral image data are now described in more detail with respect to FIGS. 4-7.

The apparatus implements an algorithm that, in summary, does the following:

The algorithm takes K spectral input image volumes and decomposes them linearly into M material image volumes. Unlike other approaches, the number of input and material images is not limited to e.g. K=2 or M=2. Unlike other approaches, the decomposition is not independent for each voxel, but considers neighborhood relations (e.g. gradients).

The material images are manipulated in a material-specific way (e.g. the tagged material component may be erased or diminished). Specific topological constraints are applied, and morphological operations using anatomical shape priors are applied.

The K spectral input image volumes are re-composed from the M material images. The re-composed images can are improved (with respect to a specific application) by the manipulation in step (2).

Thus for example, three input volume/image data sets could be 80 kV image data, 120 kV image data and non-energy resolved image data in this case K=3 but there can be more input data sets, where for example multispectral data has more than 2 energy bands such as 3, 4 and even 12 or more for future multispectral systems. Additionally, rather than 80 kV image data and 120 kV image data being used as input, the input can be for example Compton scattering image data and Photoelectric effect image data with an attenuation image for example. Moreover, also additional derived volumes can be added, such as the result of an edge-preserving smoothing of one or more of the energy-resolved volumes to help with regularization.

Data at each point in an imaged object can be represented as a linear combination of basis materials—for example Water, iodine, PMMA—or other basis materials. Therefore, continuing with the above example the 80 kV data at a point (location or voxel) in an imaged object can be represented as C1*m1(80)+C2*m2(80)+C3*m3(80)+C4*m4(80)+offset (80). Where m1, m2, m3, and m4 are basis materials and C1, C2, C3 and C4 are in effect the amount of that material at that point in the imaged object. Therefore, in this instance there are four materials, M=4, and an extra offset; thus M+1=(5) values. Similarly the 120 kV data at that point in the imaged object can be represented as C1*m1(120)+C2*m2(120)+C3*m3(120)+C4*m4(120)+offset(120). Thus again we have M+1=(5) values. Similarly for the third K data set—the non-energy resolved data—the data can be similarly represented. Therefore, the total number of values is K*(M+1)=15 values for that point in the imaged object.

Thus in this case, where K=3, there are 3 linear equations that describe the 80 kV data, the 120 kV data and the non-energy resolved data at a point in the imaged object, where C1, C2, C3 and C4 are the same in each set of equations but the m values and offsets are different.

Detailed Description of Workflow of the Algorithm

Each image voxel value I of a spectral input image $k \in K$ is formulated as a linear combination of material concentration $c_i$ with $i \in K$ $$I^k = m_a^k c_a + m_s^k c_s + m_t^k c_t + m_c^k$$

where m are non-voxel-specific material coefficients, i.e. the density which a certain concentration c of a material contributes to a certain spectral image type k. A number of K×(M+1) material coefficients are required.

The formula above gives an example with the materials air ($m_a$), soft-tissue ($m_s$) and contrast-tagged ($m_t$), and an additive constant ($m_c$) (sometimes called the DarkCurrent or DC-component of an image).

Without loss of generality we can set the density of air can be set to zero:

$$m_a^k = 0$$

and an arbitrary number of M can be introduced materials:

$$I^k = m_c^k + \sum_{i=0}^{M} m_i^k c_i$$

Figure 4:
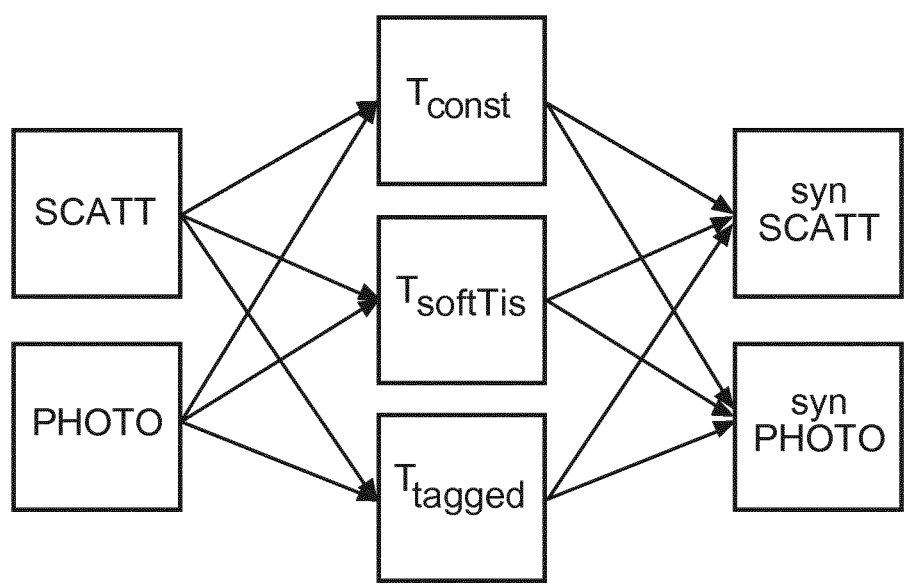
FIG. 4 shows schematically, multispectral input images on the left, decomposed material images at the center (here termed T for tissue), and on the right re-composed (or synthesized) images.
Figure 5:
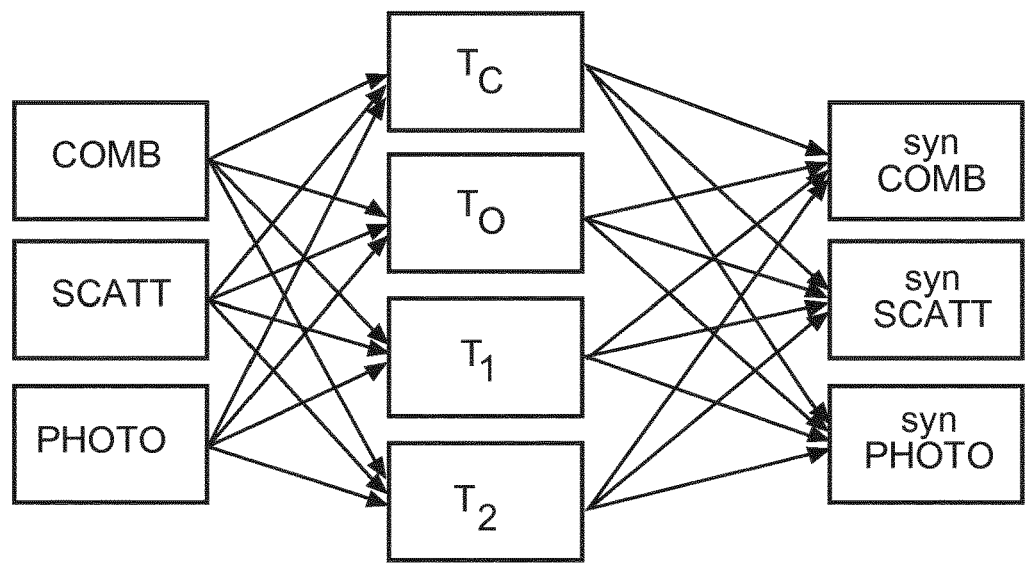
FIG. 5 shows schematically three more examples of possible configurations of spectral input images, decomposed material images, and re-composed (synthesized) spectral images.
Figure 5:
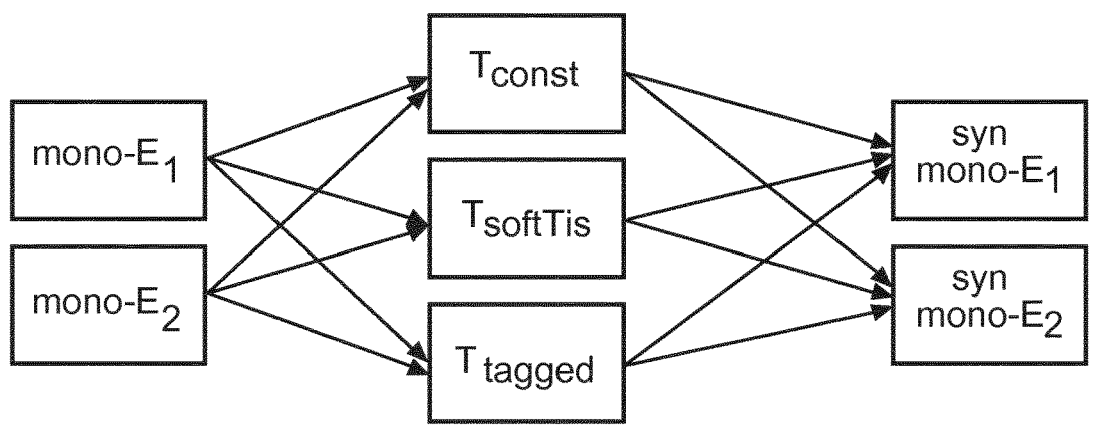
Figure 5:
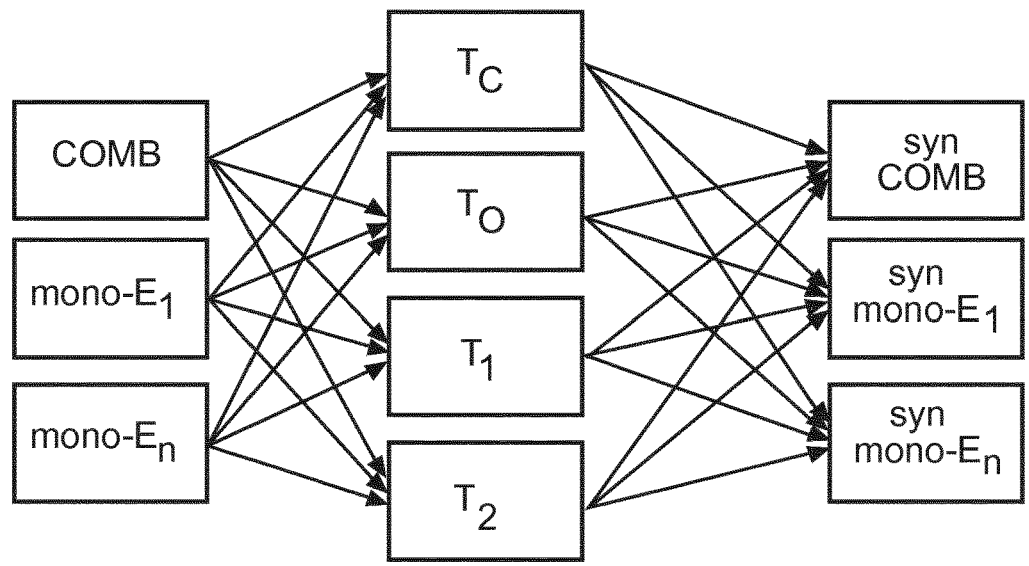

In general, the spectral input images can be any combination of conventional (combined) image, photo-effect, image, scatter-effect image, and mono-energy images (FIG. 4-5).

The algorithm starts with an initial guess for the material coefficients (e.g. values from the literature or from the last decomposition) which have K×(M+1) values.

For each voxel the composition (or concentration) vector $c_i$ is derived by solving the K linear equations from. There are M unknowns to solve for each voxel. (In case this system of equations is underdetermined, arbitrarily selected materials can be set to c=0.)

Figure 6:
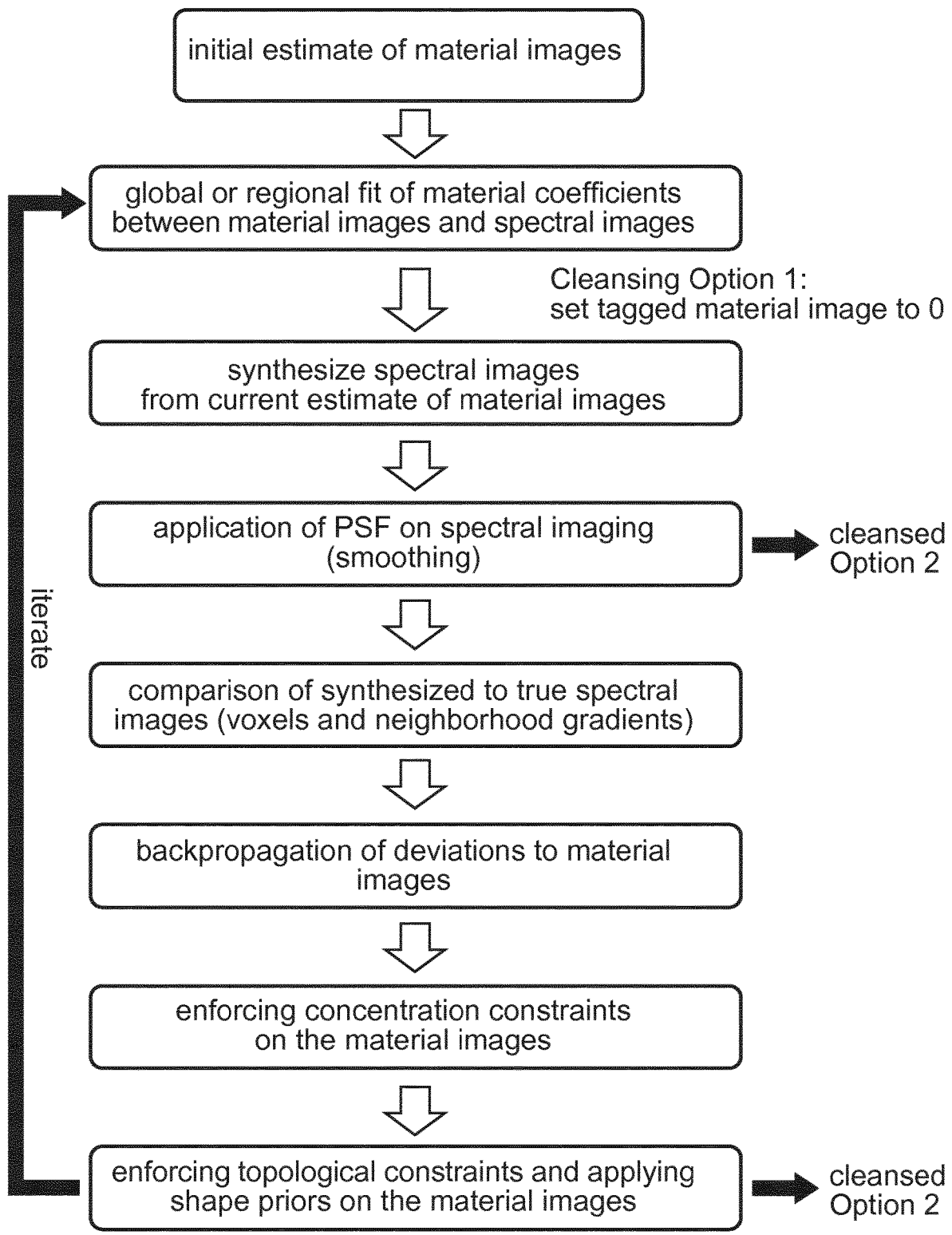
FIG. 6 shows a detailed workflow of iterative decomposition and material coefficient estimation.

This yields an initial guess for the material images (first entry in flow chart FIG. 6). Alternatively, such an initial guess of the material images can be established by considering uniquely determined voxels which are very high or low in certain spectral images, such as essentially pure air or pure contrast material, which can be set to 1 in the respective material images, and all other values to 0.

In general, each material image contains the concentration value c=0 . . . 1 for each voxel.

For all voxels together (or, alternatively, for large image regions), the linear system of equations are solved for the material coefficients $m_i^k$. Here there are a large number of N equations from N voxels, but only few K×(M+1) unknowns, so that a global least-square deviation (or L1-norm) best fit can be found efficiently.

Spectral images are synthesized from the current estimate of material images, using the current estimate of the material coefficients and the linear combination for each voxel of each spectral image.

Application of PSF to each synthesized spectral image (e.g. by a Gaussian smoothing). The scanner used to acquire the multispectral and attenuation data has a limited spatial resolution, which can be represented as a point spread function (PSF). This means that the equations are no longer truly linear for each voxel, because neighboring voxels spill into each other. The PSF is therefore simulated in forward modeling by applying a Gaussian smoothing to the synthesized energy images (rather than to try to deconvolve the observed energy images).

Comparison of the synthesized to the original spectral images k∈K yields a deviation $\Delta t^k$ for each voxel. This computation of the deviation between synthesized to original values for ever spectral image is done for every voxel, but can (optionally) be carried out additionally for all gradients between neighboring voxels and the central voxel. Here, the discrepancy between original and synthesized gradients are computed. Each gradient discrepancy is attributed to the central voxel.

If the material images are correctly hypothesized, then they should not only be able to 'explain' the observed intensities, but also the observed gradients between the voxels. Therefore the gradients can compared, too, in addition to the intensities.

Let the observed gradient g(x, x') between a voxel at positon x and its neighbor at position x' be $$g(x,x')=o(x)-o(x')$$

where o is the observed intensity in a certain spectral image k. Then it is expected that the synthesized intensity s should be equal to the synthesized neighbor intensity s(x') plus the observed gradient.

$$s(x)!=s(x')+g(x,x')$$

Any deviation from equality s(x)−(s(x')+g(x,x')) is therefore back-projected as a correction Ds to the central voxel s(x):

$$Ds=-\text{gamma}^*(s(x)-(s(x')+g(x,x')))$$

This correction translates to a certain material i proportional to the current material coefficient estimate m $$Dc_i=-\text{gamma}^*(s(x)-(s(x')+g(x,x')))^*m_i$$

The synthesized intensities should be equal to the observed intensities. Therefore, if a synthesized intensity is too high, the material concentration estimate should be lowered, and vice versa. Furthermore, the material concentration should be changed in proportion to the material coefficient m. The correction step is applied with only a small constant gamma, in order to enable a numerically stable slow convergence.

The situation explained, in summary at point 5, is now explained in more detail. Backpropagation of the deviations (discrepancies) $D^k = I_{syn}^k - I_0^k$ for each voxel to each of the material images k is done by following the negative direction of the gradient $\nabla D^k = (\partial D^k / \partial c_i)$, the components of which consist of the partial derivatives with respect to the concentrations $c_i$:

$$\partial D^k / \partial c_i = \partial (I_{syn}^k - I_0^k) / \partial c_i$$
$$= \partial I_{syn}^k / \partial c_i$$
$$= \partial \left( m_i^k c_i + \sum_{i=0}^{M} m_i^k c_i \right) / \partial c_i$$
$$= m_i^k$$

Then each concentration is iteratively updated with $$c_i \to c_i + \Delta c_i$$
$$\Delta c_i = -\gamma \cdot D^k \cdot \partial D^k / \partial c_i$$
$$= -\gamma \cdot D^k \cdot m_i^k$$

The concentration constraint $c_i \geq 0$ and $\Sigma c_i \leq 1.0$ is enforced on the material images; i.e., if the sum over concentrations $c_i$ is larger than 1.0, then divide all $c_i$ by $\Sigma c_i$.

Material specific topological constraints are enforced on the material images. (E.g., the soft tissue must be a topologically simple connected component. Thus 'free floating' islands of soft tissue is not anatomically plausible; also no holes (handles) are plausible.) Material specific morphological operations are applied on the material images. (E.g. applying edge-preserving smoothing, removing thin transition layers, emphasizing anatomical shape priors, filtering of certain spatial frequency components, etc.). E.g. at each step of the iteration, the colon wall image volume, which is one of the material volumes, is analyzed with respect to connected components. The condition is that the colon wall is a single connected component. If there are more isolated components, then all components except for the largest one are erased, i.e. the material concentration values set to zero, for the next iteration.

Iterate this process, re-starting at step (1), until convergence, i.e. small mean shift of the material images and material coefficients.

Figure 7:
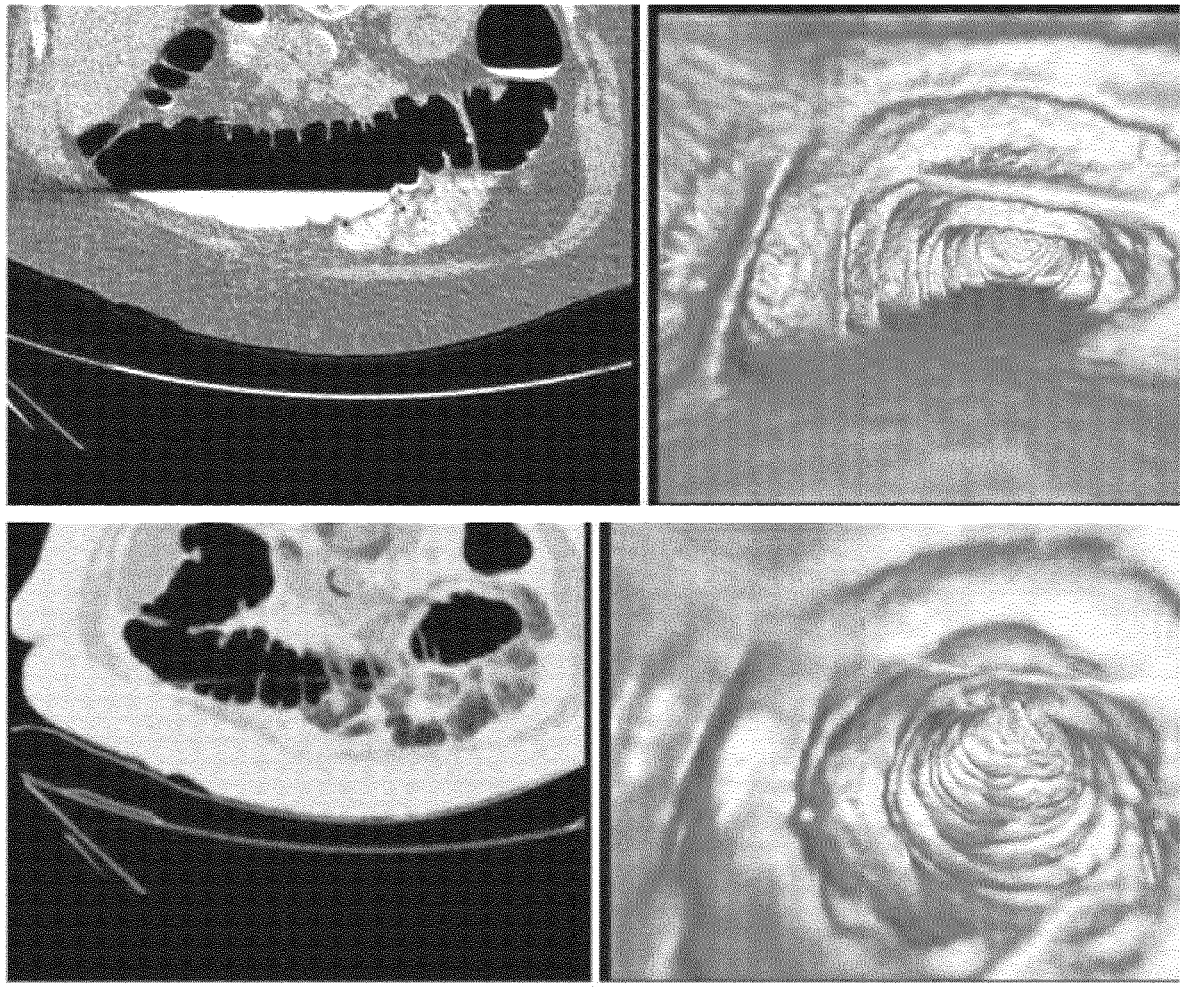
FIG. 7 shows at the top on the left a conventional image and on the right a volume rendering showing tagged fluid as an opaque surface, and at the bottom a virtually (electronically) cleansed material image, with volume rendering on the right at the same position showing the cleansed colon wall beneath the tagged fluid layer.

There are two options to get a cleansed image as an input for a volume rendering for virtual endoscopic rendering (FIG. 7).

Taking one of the synthesized spectral images after the material image for contrast tagged material has been cleared (set to 0 for all voxels).

Taking one of the material images (or an appropriate linear combination of material images) other than the tagged-material-image (e.g. the soft-tissue material image).

The Above Approach Provides the Following Advantages

The iterative approach allows to consider not only partial volume effects (PVE, within one voxel), but moreover to include neighborhood conditions and operations (gradients, point spread function (PSF), anatomical shape priors, topological constraints).

An arbitrary number of multispectral input image types can be used (e.g. conventional image, photo-effect image, scatter-effect image, noise-image, arbitrary virtual monoenergetic images), which may add non-redundant information.

The multispectral input can be decomposed into an arbitrary number of material images (because the neighborhood contains additional information).

The refined material decomposition leads to improved electronic cleansing.

The algorithm allows massively parallel implementation (e.g. on GPUs).

In another exemplary embodiment, a computer program or computer program element is provided that is characterized by being configured to execute the method steps of the method according to one of the preceding embodiments, on an appropriate system. The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for iterative material decomposition of multispectral image data, comprising:
    an input configured to provide a) a plurality of spectral images of a region of interest comprising a body part and b) a plurality of sets of material coefficients for a plurality of materials, wherein for a set of material coefficients each material coefficient is associated with a corresponding material, and wherein each set of material coefficients is associated with a corresponding spectral image of the plurality of spectral images;
    at least one processor configured to:
        i) decompose each spectral image of the plurality of spectral images into a plurality of material images and an offset image, wherein different material images correspond to different materials of the plurality of materials, and wherein a material image is represented by the material coefficient for the corresponding material multiplied by material concentrations at different image locations, and wherein the material coefficient is one of the material coefficients from the set of material coefficients for the corresponding spectral image;
        ii) manipulate at least one of the material images for each spectral image on the basis of at least one topological constraint relating to the body part to determine for each spectral image an updated plurality of material images and an updated offset image;
        iii) recompose a plurality of spectral images, wherein each recomposed spectral image is recomposed from the corresponding updated plurality of material images and the updated offset image;
        iv) compare intensities at image locations in a recomposed spectral image to the intensities at the image locations in its corresponding spectral image prior to recomposition to determine a plurality of corrections, wherein a correction is associated with an image location;
        v) modify the updated plurality of material images for each spectral image comprising utilization of the corresponding plurality of corrections;
        vi) iterate ii) to v) until convergence; and
    an output configured to output at least one of the recomposed spectral images at convergence and/or output at least one of the updated material images at convergence.

2. The apparatus according to claim 1, wherein each spectral image of the plurality of spectral images is decomposed into a linear combination of the plurality of material images and the offset image.

3. The apparatus according to claim 1, wherein an offset associated with a first spectral image is different to an offset associated with a second spectral image.

4. The apparatus according to claim 1, wherein the at least one processor is configured to apply Gaussian smoothing to the recomposed plurality of spectral images.

5. The apparatus according to claim 1, wherein the at least one processor is configured to analyze the at least one of the material images for each spectral image to determine connected components, and wherein the at least one topological constraint relating to the body part comprises that the body part is comprised of at least one connected component.

6. The apparatus according to claim 5, wherein the at least one connected component is a single connected component.

7. The apparatus according to claim 5, wherein manipulation of the at least one of the material images on the basis of the at least one topological constraint comprises setting material coefficients other than those for the at least one connected component to zero.

8. The apparatus according to claim 5, wherein manipulation of the at least one of the material images on the basis of the at least one topological constraint comprises setting material coefficients other than those for the largest connected component to zero.

9. The apparatus according to claim 1, wherein the at least one processor is configured to calculate a plurality of gradients between intensities at a corresponding plurality of locations in the spectral image prior to recomposition, and wherein the at least one processor is configured to utilize the plurality of gradients with the recomposed spectral image to determine a plurality of gradient derived corrections, and wherein modification of the updated plurality of material images for each spectral image comprises utilization of the corresponding plurality of gradient derived corrections.

10. The apparatus according to claim 9, comprising determination of a plurality of gradients in intensity between a plurality of first locations and a plurality of second locations in the spectral image prior to recomposition and application of the plurality of gradients to the plurality of first locations in the recomposed spectral image to determine a plurality of gradient derived intensities at the plurality of second locations in the recomposed spectral image, and wherein determination of the plurality of gradient derived corrections comprises a comparison of the plurality of gradient derived intensities at the plurality of second locations in the recomposed image with a plurality of intensities at the plurality of second locations in the recomposed spectral image.

11. The apparatus according to claim 10, wherein the comparison of the plurality of gradient derived intensities at the plurality of second locations in the recomposed image with the plurality of intensities at the plurality of second locations in the recomposed spectral image comprises a subtraction of the gradient derived intensities at the plurality of second locations in the recomposed image from the plurality of intensities at the plurality of second locations in the recomposed spectral image to provide a plurality of intensity corrections, and wherein modification of the updated plurality of material images for each spectral image comprises correcting the plurality of intensities at the plurality of first positions in the recomposed image by the corresponding plurality of intensity corrections and multiplication of the corrected intensities by the material coefficient for each material image of the updated plurality of material images for each spectral image.

12. The apparatus according to claim 1, wherein decomposition of each spectral image of the plurality of spectral images into a plurality of material images and the offset image comprises the enforcement of a concentration constraint such that the summation of material concentrations at a location in the plurality of spectral images is less than or equal to one.

13. A method for iterative material decomposition of multispectral image data, comprising:
a) providing a plurality of spectral images of a region of interest comprising a body part;
b) providing a plurality of sets of material coefficients for a plurality of materials, wherein for a set of material coefficients each material coefficient is associated with a corresponding material, and wherein each set of material coefficients is associated with a corresponding spectral image of the plurality of spectral images;
c) decomposing each spectral image of the plurality of spectral images into a plurality of material images and an offset image, wherein different material images correspond to different materials of the plurality of materials, and wherein a material image is represented by the material coefficient for the corresponding material multiplied by material concentrations at different image locations, and wherein the material coefficient is one of the material coefficients from the set of material coefficients for the corresponding spectral image;
e) manipulating at least one of the material images for each spectral image on the basis of at least one topological constraint relating to the body part to determine for each spectral image an updated plurality of material images and an updated offset image;
f) recomposing a plurality of spectral images, wherein each recomposed spectral image is recomposed from the corresponding updated plurality of material images and the updated offset image;
g) comparing intensities at image locations in a recomposed spectral image to the intensities at the image locations in its corresponding spectral image prior to recomposition to determine a plurality of corrections, wherein a correction is associated with an image location;
i) modifying the updated plurality of material images for each spectral image comprising utilization of the corresponding plurality of corrections;
j) iterating e) to i) until convergence; and
k) outputting at least one of the recomposed spectral images at convergence and/or output at least one of the updated material images at convergence.

14. A non-transitory computer-readable medium having executable instructions stored thereon which, when executed by at least one processor, cause the at least one processor to perform the method according to claim 13.

* * * * *